United States Patent [19]
Mayer et al.

[11] Patent Number: 5,990,306
[45] Date of Patent: Nov. 23, 1999

[54] PROCESS FOR THE PURIFICATION OF CAPROLACTAM OBTAINED FROM THE DEPOLYMERIZATION OF POLYAMIDE-CONTAINING CARPET

[75] Inventors: Richard Eugene Mayer, Richmond; Lamberto Crescentini, Chester; Theodore John Jenczewski, Midlothian, all of Va.

[73] Assignee: AlliedSignal Inc., Morristown, N.J.

[21] Appl. No.: 08/922,853

[22] Filed: Sep. 3, 1997

[51] Int. Cl.$^6$ ................................................ C07D 201/12
[52] U.S. Cl. ............................................................ 540/540
[58] Field of Search ............................................ 540/540

[56] References Cited

U.S. PATENT DOCUMENTS

| | | | |
|---|---|---|---|
| 2,813,858 | 11/1957 | Joris | 260/239.3 |
| 3,406,176 | 10/1968 | Surrey et al. | 260/287 |
| 3,939,153 | 2/1976 | Fowler | 260/239.3 |
| 4,107,160 | 8/1978 | Dicoi et al. | 260/239.3 |
| 4,148,792 | 4/1979 | Danziger et al. | 260/239.3 |
| 4,148,793 | 4/1979 | Danziger et al. | 260/239.3 |
| 4,170,592 | 10/1979 | Danziger et al. | 260/239.3 |
| 4,178,287 | 12/1979 | Mattone et al. | 260/239.3 |
| 4,248,781 | 2/1981 | Horn et al. | 260/239.3 |
| 4,301,073 | 11/1981 | Fuchs et al. | 260/239.3 |
| 4,314,940 | 2/1982 | Senni et al. | 260/239.3 |
| 4,326,925 | 4/1982 | Senni et al. | 203/37 |
| 4,328,154 | 5/1982 | Senni et al. | 260/239.3 |
| 4,457,807 | 7/1984 | Rulkens et al. | 203/72 |
| 4,493,719 | 1/1985 | Wintermantel et al. | 62/532 |
| 4,582,642 | 4/1986 | Crescentini et al. | 260/239.3 |
| 4,605,762 | 8/1986 | Mandoki | 562/483 |
| 4,606,858 | 8/1986 | Bondi et al. | 540/540 |
| 4,610,768 | 9/1986 | Moosavian | 203/14 |
| 4,720,328 | 1/1988 | Corbin et al. | 203/37 |
| 4,767,503 | 8/1988 | Crescentini et al. | 203/48 |
| 4,795,571 | 1/1989 | Holzknecht et al. | 210/774 |
| 4,882,430 | 11/1989 | Neubauer et al. | 540/540 |
| 4,900,821 | 2/1990 | Tan et al. | 540/540 |
| 5,032,684 | 7/1991 | Neubauer et al. | 540/540 |
| 5,169,870 | 12/1992 | Corbin et al. | 521/49.8 |
| 5,233,037 | 8/1993 | Nielinger et al. | 540/540 |
| 5,241,066 | 8/1993 | Davis et al. | 540/540 |
| 5,245,029 | 9/1993 | Inaba et al. | 540/540 |
| 5,350,847 | 9/1994 | Fuchs et al. | 540/540 |
| 5,359,062 | 10/1994 | Fuchs | 540/540 |
| 5,440,032 | 8/1995 | Hirosawa et al. | 540/540 |
| 5,441,607 | 8/1995 | Fuchs et al. | 203/49 |
| 5,455,346 | 10/1995 | Kopietz et al. | 540/540 |
| 5,457,197 | 10/1995 | Sifniades et al. | 540/540 |
| 5,458,740 | 10/1995 | Losier et al. | 203/34 |
| 5,495,014 | 2/1996 | Fuchs et al. | 540/538 |
| 5,495,015 | 2/1996 | Bassler et al. | 540/540 |
| 5,502,184 | 3/1996 | Kajikuri et al. | 540/536 |
| 5,536,831 | 7/1996 | Kopietz et al. | 540/540 |
| 5,539,106 | 7/1996 | Thijeert et al. | 540/540 |
| 5,556,890 | 9/1996 | Halderit et el. | 521/49.8 |
| 5,637,700 | 6/1997 | Fuchs et al. | 540/540 |
| 5,656,757 | 8/1997 | Jenczewski et al. | 540/540 |
| 5,681,952 | 10/1997 | Sifniades et al. | 540/540 |

FOREIGN PATENT DOCUMENTS

| | | |
|---|---|---|
| 08048666 | 2/1996 | Japan . |
| 80 48666 | 2/1996 | Japan . |
| 67725 | 7/1973 | Poland . |
| 72745 | 12/1974 | Poland . |
| 82269 | 8/1976 | Poland . |
| 89233 | 6/1977 | Poland . |
| 238550 | 6/1969 | U.S.S.R. . |
| WO 94/06763 | 3/1994 | WIPO . |
| WO 97/20813 | 6/1997 | WIPO . |
| WO 97/34868 | 9/1997 | WIPO . |

OTHER PUBLICATIONS

J. Synowiec et al., "Oczyszczanie Kaprolaktamu przez krystalizacje z roztworu wodnego", *Przemys Chemiczny* 57(4), pp. 185–189 (1978).

Encyclopedia of Chemical Technology, vol. 4, Kirk–Othmer, "Caprolactam", pp. 830–832.

L.A. Dmitrieva et al., "Regeneration of $\epsilon$–Caprolactam from Wastes in the Manufacture of Polycaproamide Fibres and Yarns", *Fibre Chemistry 17(4)*, 229 (Mar. 1986).

K.V. Datye, "Recycling Processes and Products in Nylon 6 Fibre Industry", *Indian Journal of Fibre & Textile Research 16*, 46 (Mar. 1991).

N.D. Sharma, "Utilization of Polycaproamide (Nylon–6 Waste)", *Textile Asia,* 66 (1991).

"Caprolactam Recovery from Carpets by Polyamide 6 Recycling", IFJ, 34 (Oct. 1992).

*Primary Examiner*—Mukund J. Shah
*Assistant Examiner*—Bruck Kifle
*Attorney, Agent, or Firm*—Melanie L. Brown; Virginia S. Andrews; Roger H. Criss

[57] ABSTRACT

The present invention provides a process for the preparation of purified caprolactam comprising the steps of:

(a) depolymerizing polyamide-containing carpet in the presence of steam to obtain crude caprolactam and steam;

(b) removing substantially all of said water from said crude caprolactam and steam (c) distilling the resulting concentrated crude caprolactam at a pressure of less than about 8 mmHg and a temperature from about 110° C. to about 145° C. so as to form overheads and bottoms of the caprolactam; and (d) crystallizing the caprolactam overheads to obtain caprolactam crystals and mother liquor.

The resulting purified caprolactam may then be used to make polycaprolactam which may then be used in engineered materials or spun into fiber.

19 Claims, 3 Drawing Sheets

PROCESS FOR THE PURIFICATION OF CAPROLACTAM OBTAINED FROM THE DEPOLYMERIZATION OF POLYAMIDE-CONTAINING CARPET

The present invention relates to a process for the purification of caprolactam obtained from the depolymerization of polyamide-containing carpet.

BACKGROUND OF THE INVENTION

One method for the preparation of caprolactam involves the liquid-phase catalytic hydrogenation of phenol to form cyclohexanone, the reaction of formed cyclohexanone with hydroxylamine sulfate to produce cyclohexanone oxime, and Beckmann rearrangement of the formed cyclohexanone oxime with oleum to form crude caprolactam according to Kirk-Othmer Encyclopedia of Chemical Technology 4, 830–832 (1992). Typical impurities in such crude caprolactam are benzene, cyclohexanone oxime, aniline, octahydrophenazine, acetic acid, phenol, adipimide, ammonium benzenesulfonate, ammonium 3-cyclohexanone sulfonate, and ammonium 2-hydroxycyclohexanone sulfate. Methods for purifying such crude caprolactam include oxidation as taught by U.S. Pat. Nos. 4,148,792; 4,178,287; 4,248,781; 4,314,940; 4,720,328; 5,350,847; and 5,637,700; extraction as taught by U.S. Pat. Nos. 4,148,793; 4,170,592; 4,301,073; and 4,606,858; ion exchange as taught by U.S. Pat. Nos. 5,245,029 and 5,440,032; hydrogenation as taught by U.S. Pat. Nos. 5,032,684; 5,502,184; and 5,539,106; crystallization as taught by U.S. Pat. Nos. 4,493,719; 4,795,571; 4,882,430; 4,900,821; and commonly assigned U.S. Pat. No. 2,813,858; and distillation as taught by U.S. Pat. Nos. 4,326,925; 4,328,154; 4,457,807; 4,610,768; 5,441,607; 5,458,740; and commonly assigned 4,767,503.

Another method for the preparation of caprolactam involves depolymerization of nylon production scrap as taught by U.S. Pat. Nos. 3,939,153; 4,605,762; 5,233,037; 5,241,066; 5,359,062; and 5,495,014. U.S. Pat. No. 5,458,740 teaches that the wastewater from the polymerization of caprolactam contains polycaprolactam which may be depolymerized and the resulting caprolactam may then be purified by adding inorganic acid such as sulfuric acid to caprolactam and water mixture and distilling at 666–1066 Pa and between 165–180° C. However, the use of sulfuric acid is disadvantageous because the sulfuric acid may catalyze the formation of aminocaproic acid and oligomers.

Recently, methods have been developed for the depolymerization of waste nylon-containing carpet as taught by commonly assigned U.S. Pat. No. 5,457,197 and U.S. Pat. No. 5,681,952. International Publication WO97/20813, which claims priority from U.S. Pat. No. 5,681,952 teaches a process for depolymerizing multicomponent waste material comprising polycaprolactam and non-polycaprolactam components to form caprolactam. The process comprises the step of: in the absence of added catalyst, contacting the multi-component waste material with superheated steam at a temperature of about 250° C. to about 400° C. and at a pressure within the range of about 1 atm to about 100 atm and substantially less than the saturated vapor pressure of water at the temperature wherein a caprolactam-containing vapor stream is formed. The reference teaches that caprolactam may be separated from other components of the distillate by sending the vapors from the reactor overhead to a partial condenser to obtain a condensate containing caprolactam. The reference also teaches that fiber grade caprolactam may be obtained from this condensate by further purification including distillation, crystallization, and other conventional techniques known in the art and that for example, the caprolactam purification process of AlliedSignal's U.S. Pat. Nos. 2,813,858; 3,406,176 or 4,767,503 to Crescentini et al. may be used.

Example 8 of U.S. Pat. No. 5,681,952 teaches that the crude caprolactam was submitted to fractional distillation under vacuum and a fraction containing over 99% caprolactam was obtained and that less than 10% of the available caprolactam remained in the distillation bottoms. The distilled caprolactam was further purified via crystallization from water to yield fiber quality caprolactam.

Carpets include a face fiber that is adhered to a support material such as jute or polypropylene backing, latex (such as a styrene-butadiene rubber (SBR)), and a variety of inorganic materials such as calcium carbonate, clay, or hydrated alumina fillers. Nylon 6 is often used for the face fiber. Typically, carpet comprises about 20–55 percent by weight face fiber and 45–80 percent by weight backing materials. In addition, the fiber contains dyes, soil repellents, stabilizers, and other compounds added during fiber and/or carpet manufacture. Waste carpet may also contain a host of other impurities, which will collectively be referred to herein as "dirt". Decomposition products including 6-aminohexanoic acid; caprolactam dimer; N-methylcaprolactam; N-ethylcaprolactam; hexenoic acid; cyclohexylamine; hexamethylene diamine (HMDA); and acetic acid; and non-nylon-6 derived components such as 1,3-diphenylpropane; styrene dimer; styrene-butadiene oligomers; and acids, aliphatic alcohols such as 1-decanol and 1-dodecanol and carboxylic acids with 6 to 16 carbon atoms per molecule contaminate the depolymerized polycaprolactam and need to be removed in order to obtain world class caprolactam. The term "world class caprolactam" as used herein means caprolactam having a purity greater than 99.9 weight percent (excluding water) and a permanganate number less than 3 and a color number less than 2.

U.S. Pat. No. 5,169,870 and International Publication WO94/06763 teach the depolymerization of nylon-6 carpet in the presence of phosphoric acid and steam to form crude caprolactam which is first purified by condensing and fractionating volatile components from the crude caprolactam. Potassium permanganate is then added to the resulting crude caprolactam and water mixture wherein the permanganate oxidizes the impurities which are not removed in the fractionation step. This method is disadvantageous according to U.S. Pat. Nos. 5,556,890 and 5,637,700 because solid manganese dioxide is produced during the purification which then has to be removed from the reaction by means of filtration. See also U.S. Pat. Nos. 5,455,346; 5,495,015; and 5,536,831. U.S. Pat. No. 5,556,890 teaches that depolymerized nylon-6 carpet may be purified by hydrogenation in the presence of a hydrogenation catalyst. Hydrogenation is a disadvantageous process because it requires a capital intensive step and rather than lower the total impurities, hydrogenation only changes the impurities to another substance.

A need in the art exists for a process for purifying caprolactam obtained from the depolymerization of polyamide-containing carpet which avoids the preceding problems in the art. We depolymerized polyamide-containing carpet and then attempted to purify it by crystallization alone. Unfortunately, crystallization produced poor quality crystals which could not be washed adequately and the purity of the resulting caprolactam was unsuitable for commercial use as reported in Comparative Example 1 below. We also depolymerized waste nylon-containing carpet and then attempted to purify it by distillation alone. The results were unacceptable as reported in Comparative Example 2 below. Example 8 of U.S. Pat. No. 5,681,952 does not teach or suggest a distillation temperature, distillation pressure, the crystallization conditions, or the final caprolactam purity.

SUMMARY OF THE INVENTION

We have developed a process for the purification of caprolactam obtained from the depolymerization of polyamide-containing carpet which responds to the foregoing need in the art. We have now found that if the crude caprolactam from depolymerization of polyamide-containing carpet is subjected to a simple flashing operation, the condensed flashed material may be crystallized from the aqueous solution and good quality, washable crystals are obtained. The resulting caprolactam has a purity greater than 99.9 weight percent (excluding water) and a permanganate number less than 3 and a color number less than 2 and thus, is world class caprolactam.

Although not wishing to be bound by theory, we believe that high boiling impurities, perhaps polycaprolactam depolymerization decomposition products such as 6-aminocaproic acid, or latex decomposition products, or original fiber additives such as dyes, prevented proper crystallization of caprolactam whereas light boiling contaminants, originally present, or formed by cracking, play only a secondary role.

Thus, the present invention provides a process for the preparation of purified caprolactam comprising the steps of:

(a) depolymerizing polyamide-containing carpet in the presence of steam to obtain crude caprolactam and steam;

(b) removing substantially all of said water from said crude caprolactam and steam;

(c) distilling the resulting concentrated crude caprolactam at a pressure of less than about 8 mmHg and a temperature from about 110° C. to about 145° C. so as to form overheads and bottoms of the caprolactam; and (d) crystallizing the caprolactam overheads to obtain caprolactam crystals and mother liquor.

The present invention is advantageous because the process lowers capital cost and does not require the use of hydrogen or oxidizing agents.

Other advantages of the present invention will be apparent from the following description, attached drawings, and attached claims.

DETAILED DESCRIPTION OF THE PREFERRED EMBODIMENT

Figure 1:
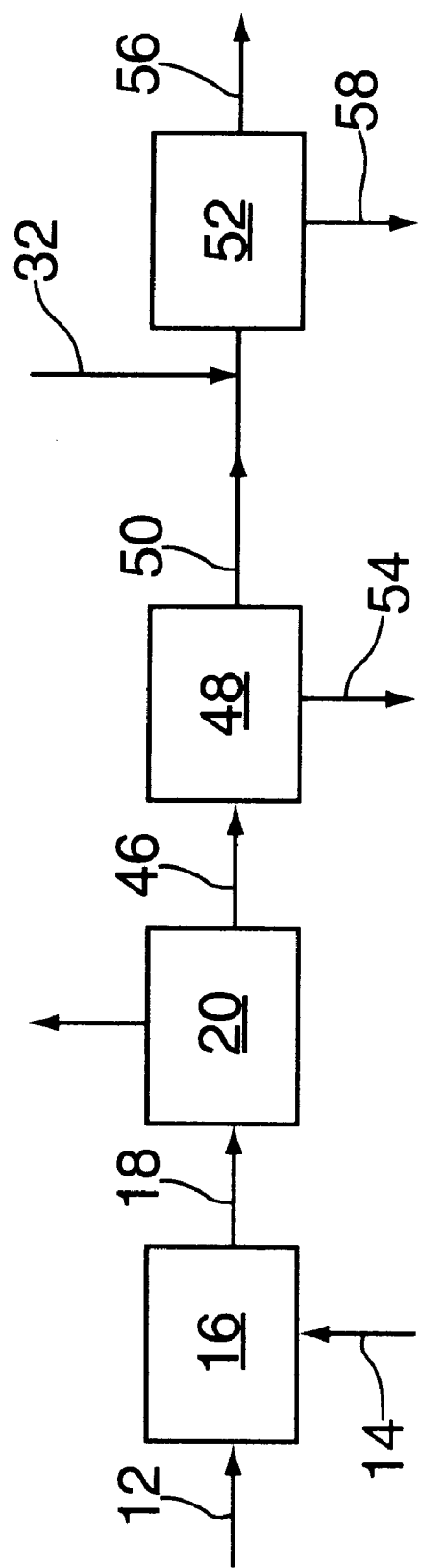
FIG. 1 illustrates the present invention.

Step (a) of the present invention is depolymerizing polyamide-containing carpet to obtain crude caprolactam as taught by commonly assigned U.S. Pat. No. 5,681,952. Preferably, step (a) comprises the step of: in the absence of added catalyst, contacting polyamide-containing carpet with superheated steam at a temperature of about 250° C. to about 400° C. and at a pressure within the range of about 1 atm to about 100 atm and substantially less than the saturated vapor pressure of water at the temperature wherein a caprolactam-containing vapor stream is formed.

The term "polyamide-containing carpet" as used herein means that carpet resulting from scrap generated during carpet manufacturing, carpet installation, or removal of installed carpet and comprising face fiber that is adhered to a support material such as jute or polypropylene backing, latex (such as a styrene-butadiene rubber (SBR)), and a variety of inorganic materials such as calcium carbonate, clay, or hydrated alumina fillers. Nylon 6 is often used for the face fiber. Typically, carpet comprises about 20–55 percent by weight face fiber and 45–80 percent by weight backing materials. In addition, the fiber contains dyes, soil repellents, stabilizers, and other compounds added during fiber and/or carpet manufacture. Waste carpet may also contain a host of other impurities, which will collectively be referred to herein as "dirt".

According to step (a) of the present invention, caprolactam is formed by contacting the polyamide-containing carpet with superheated steam at elevated temperatures and atmospheric or higher pressures and removing a vapor stream containing caprolactam from the contact region. The term "superheated steam" as used herein means steam that is heated to a temperature substantially higher than the temperature at which condensation to liquid water would take place at the pressure used to convey said steam. Because whole carpet generally includes calcium carbonate which can neutralize an acidic catalyst, an important benefit of step (a) is that no catalyst is needed.

The polyamide-containing carpet is preferably fed to the reactor as a melt. This feeding may be achieved by using an extruder, gear pump, or other means known in the art.

For step (a), the reaction temperature should be at least about 250° C. but not higher than about 400° C. Generally, the rate of caprolactam formation increases with increasing temperature. However, the rate of side reactions of nylon 6 such as evolution of ammonia also increases with temperature and so does the rate of reactions of the non-nylon 6 components of the waste polyamide-containing carpet.

For step (a), temperatures of at least about 250° C. are preferred because below 250° C., caprolactam formation may be too slow. Temperatures no greater than about 400° C. are preferred, as above 400° C. side reactions of nylon 6 and reactions of the non-nylon 6 components may become prohibitively fast. A preferred temperature range is about 280° C. to about 350° C., more preferably a temperature in the range of about 300° C. to about 340° C.

Regarding the effect of pressure, it has been found that for a given temperature and steam flow, increasing the reactor pressure generally increases the caprolactam concentration in the overheads up to an optimal pressure. Further small increases in pressure have little effect on caprolactam concentration. However, a large increase in pressure beyond the optimal pressure results in decreased caprolactam concentration. Generally, the higher the operating temperature, the higher is the optimal pressure at which maximum caprolactam concentration is obtained. For example at about 320° C. and a steam flow of 1 reaction mass per hour, the optimal pressure is about 11 atm (about 1114 kPa); at about 340° C. and a steam flow of 2.0 reaction mass per hour, the optimal pressure is about 15 atm (about 1520 kPa). Optimal pressure conditions under different operating conditions within the scope of this invention can be determined by those skilled in the art.

Commonly assigned allowed U.S. Pat. No. 5,681,952 is incorporated herein by reference.

Referring to FIG. 1, polyamide-containing carpet 12 and superheated steam 14 are fed into depolymerization reactor 16. The formed crude caprolactam-and steam stream 18 exits depolymerization reactor 16 and flows to water removal vessel 20. The term "crude caprolactam" as used herein means caprolactam and decomposition products and excludes water. The term "decomposition products" as used herein includes 6-aminocaproic acid; 6-aminohexanoic acid; caprolactam dimer; N-methylcaprolactam; N-ethylcaprolactam; hexenoic acid; cyclohexylamine; hexamethylene diamine; and acetic acid; and non-nylon-6 derived components such as 1,3-diphenylpropane; styrene dimer; styrene-butadiene oligomers; and acids, aliphatic alcohols such as 1-decanol and 1-dodecanol and carboxylic acids with 6 to 16 carbon atoms per molecule.

If the polyamide-containing carpet comprises hexamethylene diamine ("nylon 66") fibers in addition to polycaprolactam ("nylon 6") fibers, the nylon 66 depolymerization products will condense in addition to the nylon 6 depolymerization products. Although not illustrated, to prevent this, the crude caprolactam and steam stream 18 may be condensed and then passed through a strong cation exchange resin such as sulfonate resin to remove nylon 66 derived products.

If the polyamide-containing carpet comprises polypropylene carpet backing and styrene-butadiene rubber adhesive in addition to polyamide fiber, an oil is produced during the depolymerization step. Although the oil is typically insoluble in the caprolactam-water condensate, an emulsified layer which does not readily separate from the caprolactam-water condensate is usually present. This emulsified layer may be separated by adding a filter aid such as diatomaceous earth and filtering or passing it through a liquid-liquid separator.

If the polyamide-containing carpet comprises polyethylene terephthalate fibers in addition to nylon 6 fibers, the depolymerization step produces benzoic and terephthalic acids which volatilize with the lactam and water. Terephthalic acid is insoluble in water and is preferably removed to prevent difficulty in a subsequent caprolactam concentration step. By maintaining a high caprolactam concentration and then adding a strong base such as sodium hydroxide to the filtered caprolactam condensate 24 (FIG. 2), the terephthalic acid may be rendered non-volatile in distillation along with other acids.

Figure 2:
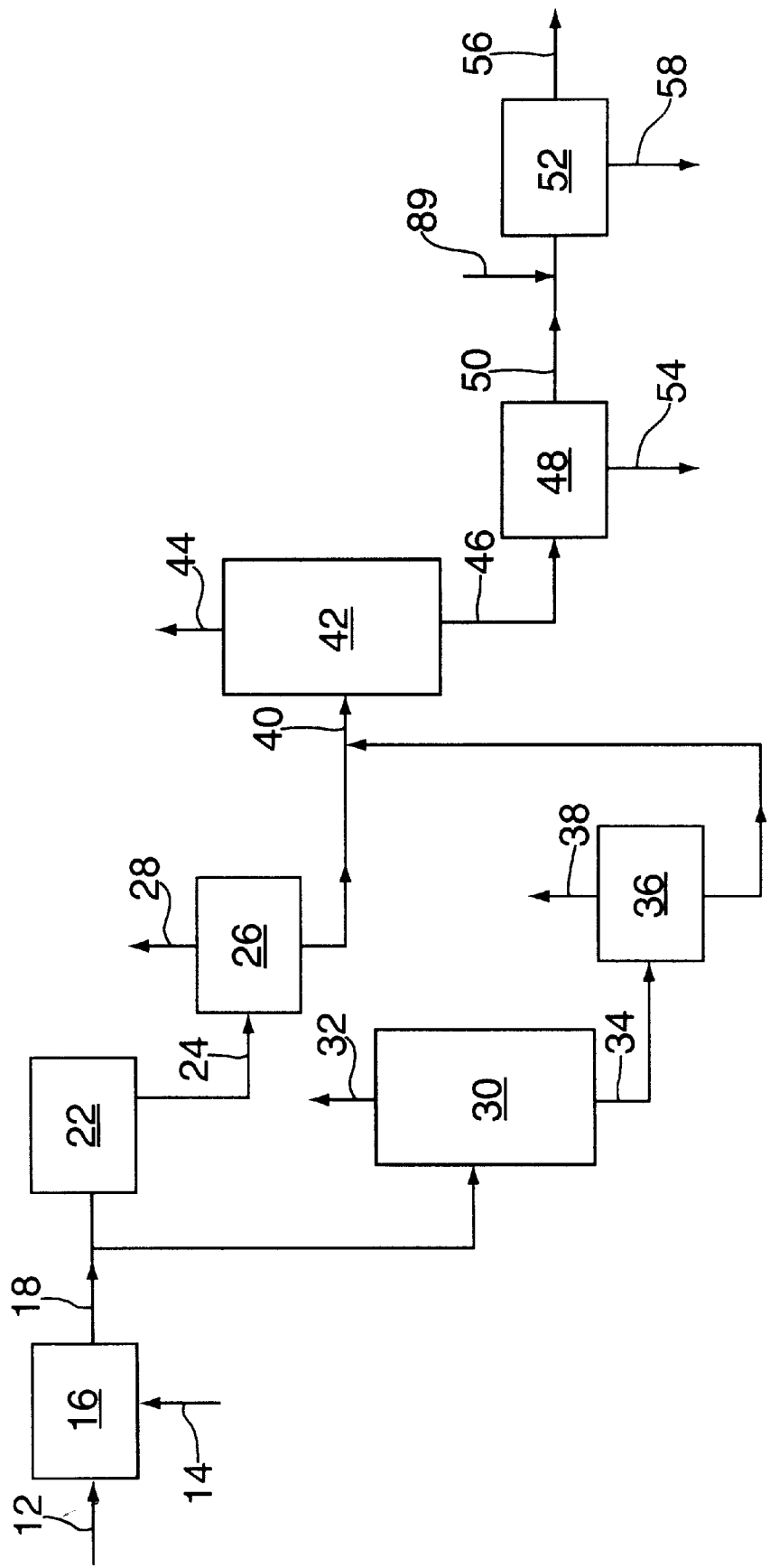
FIG. 2 illustrates different alternatives for the water removal step of the present invention.

In step (b) of the present process, water is substantially removed from the crude caprolactam and steam stream. The phrase "water is substantially removed" as used herein means the remaining crude caprolactam and water stream contains less than about 8 percent by weight water. Preferably, the remaining crude caprolactam and water stream contains less than about 6 percent by weight water. In one preferred water removal step (b)(1), the crude caprolactam and steam stream may be condensed and any oils may then separate as an upper layer insoluble in the aqueous crude caprolactam. A commercially available condenser may be used. Such operation may be performed at near ambient temperature. Referring to FIG. 2, the crude caprolactam and steam stream 18 is fed to a condenser 22 and the caprolactam condensate 24 is fed to coalescer 26. After the oils separate as an upper layer insoluble in the aqueous crude caprolactam, the oils 28 are removed from the coalescer 26.

In another preferred water removal step (b)(2), the crude caprolactam and steam stream may be fed to a distillation column where the bulk of the water is removed as an overhead stream and an aqueous crude caprolactam may be withdrawn from the distillation bottom. Oils may then separate and be removed from this aqueous solution which then may be further dewatered by distillation. A commercially available distillation column may be used. Water may be distilled at atmospheric pressure or under slight vacuum (50 Torr or above). Oils separation may be effected at near ambient temperature. Referring to FIG. 2, the crude caprolactam and steam stream 18 is fed to a distillation column 30 where the bulk of the water 32 is removed as an overhead stream and the aqueous crude caprolactam 34 is withdrawn from the distillation bottom. The aqueous crude caprolactam 34 is fed to coalescer 36. After the oils separate, the oils 38 are removed from the coalescer 36. FIG. 2 illustrates both alternative steps (b)(1) and (b)(2) so that they may be readily compared. Regardless of whether step(b)(1) or (b)(2) is practiced, the treated crude caprolactam stream 40 is fed to water flasher 42, which is operated at atmospheric pressure or under slight vacuum (50 Torr or above).

In step (c) of the present process, the resulting concentrated crude caprolactam 46 is distilled in lactam flasher 48. A commercially available lactam flasher may be used at a pressure of less than about 8 mmHg and a temperature from about 110° C. to about 150° C. so as to form overheads and bottoms of the caprolactam. If a pressure of greater than about 8 mmHg is used, the temperature is greater than 145° C. and caprolactam decomposes and results in viscous bottoms. Preferably, a pressure of less than about 8 mmHg and greater than or equal to about 2 mmHg is used. More preferably, a pressure of less than about 7 mmHg and greater than or equal to about 2 mmHg is used. Most preferably, a pressure of less than about 6 mmHg and greater than or equal to about 2 mmHg is used. If a temperature of less than 110° C. is used, the process becomes uneconomical. Preferably, a temperature from about 120° C. to about 130° C. is used. Preferably, the resulting concentrated crude caprolactam 46 is distilled to remove at least about 40 percent by weight caprolactam from the lactam flasher 48. More preferably, the resulting concentrated crude caprolactam 46 is distilled to remove at least about 60 percent by weight caprolactam from the lactam flasher 48. Referring to FIG. 1, the caprolactam distillate 50 is then fed to crystallization system 52 and the residue 54 is removed from the lactam flasher 48. The residue 54 comprises caprolactam, caprolactam oligomers, 6-aminocaproic acid, N-methylcaprolactam, N-ethylcaprolactam, hexanoic acid, hexenoic acid, 1-decanol and may, as set forth below, be further processed to separate the caprolactam from the oligomers and 6-aminocaproic acid.

In step (d) of the present process, the caprolactam distillate is crystallized by the method generally taught by commonly assigned U.S. Pat. No. 2,813,858. Preferably, the crystallization comprises the steps of: (d)(i) adding water to the caprolactam distillate 50 so that the amount of water present is at least about 2 percent by weight. A crystallization system 52 may be used. A commercially available crystallization system may be used. If less than 2 percent by weight water is added, crystallization is difficult to control and the crystals are difficult to wash. More preferably, water is added to the caprolactam distillate 34 so that the amount of water present is from about 2 to about 12 percent by weight. If more than 12 percent by weight water is added, then undesired refrigeration would have to be used Preferably, in step (d)(ii), the caprolactam/water mixture is heated to a temperature from about 35° C. to about 65° C. with agitation until the caprolactam is dissolved in the water. If a temperature less than 35° C. is used, the dissolving takes longer. If a temperature greater than 65° C. is used, too much cooling will be required later More preferably, the caprolactam/water mixture is heated to a temperature from about 40° C. to about 60° C. Preferably, in step (d)(iii), the caprolactam/water mixture is cooled to at least about 60° C. to form at least about 25 percent by weight caprolactam crystals. Alternatively, in preferred step (d)(iii), sufficient water is evaporated from the caprolactam/water mixture to form at least about 25 percent by weight caprolactam crystals. The term "crystals" as used herein means solid caprolactam granules. Referring to FIG. 1, the caprolactam crystals 56 are removed from crystallization system 52 and the mother liquor 58 is removed from crystallization system 52. The caprolactam crystals 56 may be separated from the mother liquor 58 by centrifuge or filtration. The crystals may then be washed with pure lactam or lactam solution.

Preferably, crystallization step (d) is repeated.

Commonly assigned U.S. Pat. No. 2,813,858 is incorporated herein by reference.

The term "color" as used herein means the color of the caprolactam crystals as measured by absorbance at 390 nanometers of a 50 percent weight/volume solution in water against a water reference. Lower color numbers correspond to increasingly pure samples.

Oxidizable impurities in crude caprolactam may be measured by the effects of reaction between an aqueous lactam sample solution and a dilute oxidizing agent. The term "permanganate number" as used herein is determined according to ISO 8660 (1988-04-15) which uses a 3 percent solution weight/volume of lactam in water whose pH has been adjusted to 6.5. 2 milliliters of 0.01 N potassium permanganate is added to 100 ml of the sample solution and the absorbance is measured after 10 minutes at 420 nanometers against a water reference. A reagent blank is also run and subtracted from the sample absorbance. The reaction is conducted at 25° C. Lower permanganate numbers correspond to increasingly pure samples.

The term "purified caprolactam" as used herein means caprolactam having a purity greater than 99.9 weight percent and a permanganate level less than 3 and a color less than 2.

Optionally, to increase yields, caprolactam may be recovered from crystallization mother liquors, wash liquors, and from other impurity-laden streams such as the bottoms of the initial caprolactam flashing operation, by first evaporating water, then evaporating lactam, and feeding such lactam vapors to a distillation column where close-boiling impurities with volatility slightly higher than caprolactam may be removed as an overhead stream with the bottoms being returned to crystallization.

Figure 3:
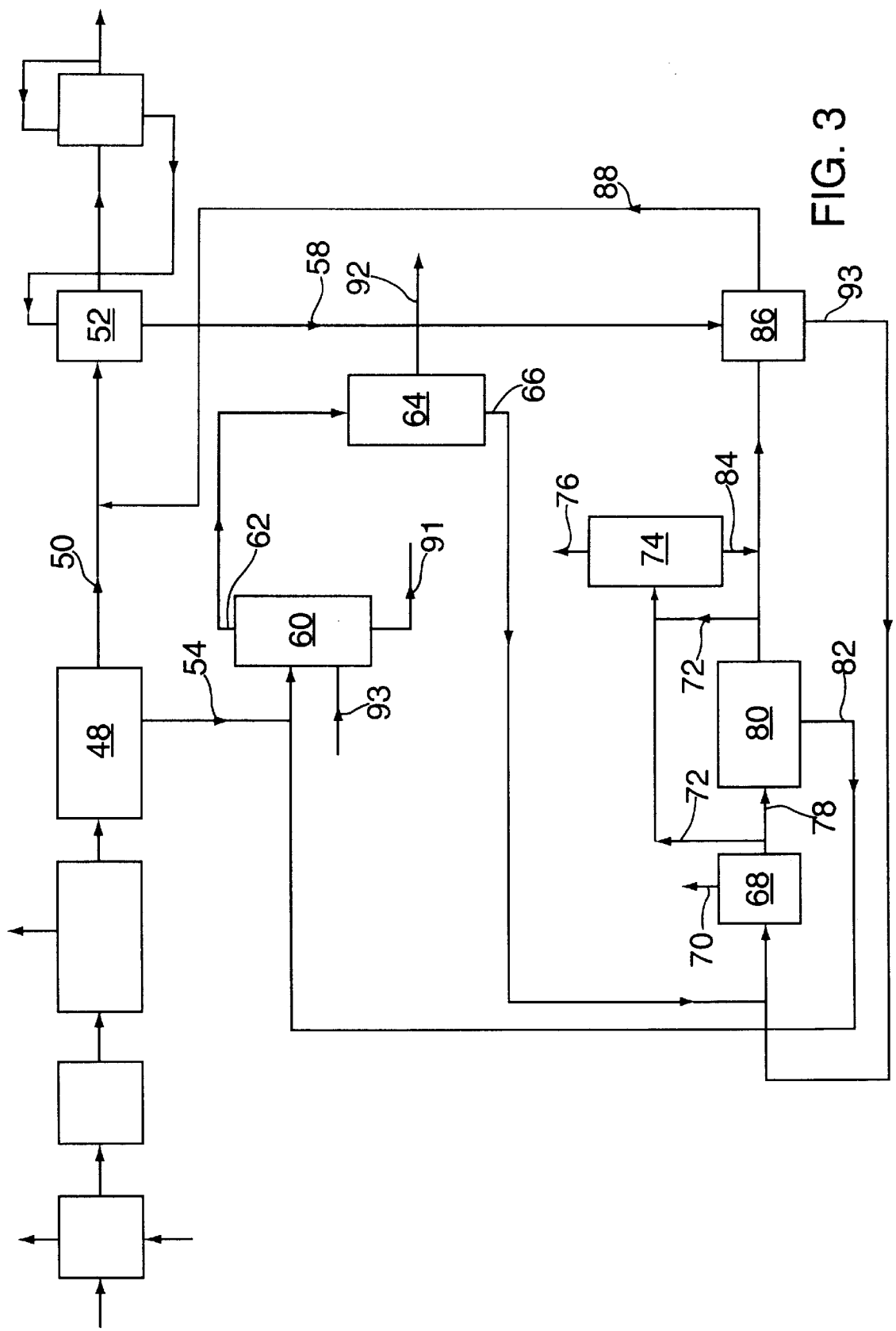
FIG. 3 illustrates an option for treatment of the mother liquor resulting from the present invention.

Preferably, to improve the purification process yield, the residue 54 may be processed so as to separate caprolactam from oligomers and 6-aminocaproic acid and thus, improve the purification process yield. Referring to FIG. 3, the residue comprising caprolactam, oligomers, 6-aminocaproic acid, diphenylpropane, styrene dimer, and styrene-butadiene oligomers 54 may be fed to a steam stripper 60 wherein the heavy impurities 54 may be steam stripped at a temperature from about 200° C. to about 300° C. with superheated steam. Because 6-aminocaproic acid may volatilize with the caprolactam and ultimately prevent crystallization, a strong base such as sodium hydroxide may be added to the steam stripper feed in order to neutralize 6-aminocaproic acid and thus, volatilization of 6-aminocaproic acid will be minimal. Alternatively, a strong acid such as sulfuric or phosphoric acid may be added to the steam stripper feed in order to neutralize 6-aminocaproic acid and thus, volatilization of 6-aminocaproic acid is minimized. If the waste polyamide-containing carpet comprises nylon 66 fiber in addition to nylon 6 fiber, nylon 66-derived products will condense in addition to nylon 6. A strong acid such as sulfuric or phosphoric acid may be added to the steam stripper feed in order to render hexamethylene diamine (HMDA) non-volatile and thus, side reactions involving HMDA are minimal. The steam stripper overheads 62 comprise caprolactam, styrene dimer, and styrene-butadiene oligomer and may be condensed. The condensate may be fed to a liquid/liquid separator 64 or coalescer to remove insoluble oils 92.

The oil-free condensate 66 may be fed to a water flasher 68 wherein water 70 may be removed. A slipstream 72 from the bottoms of the water flasher 68 or the caprolactam flasher 80 may be fed to a multistage stripper 74 where additional water and impurities which are less volatile than caprolactam plus some caprolactam (collectively shown as 76) may be removed. The water flasher bottoms 78 may flow to a lactam flasher 80 which operates at reduced pressure. About 90 percent by weight of water flasher bottoms 78 flashed goes into overheads. The lactam flasher bottoms 82 may be sent to steam stripper 60.

Bottoms 84 from multistage stripper 74 may be combined with mother liquor 58 and may be fed to purge crystallizer 86 wherein the crystals may be collected and washed on a centrifuge. The resulting crystals 88 may be combined with caprolactam distillate 50 and may serve as the feed to crystallization vessel 52. Mother liquor 93 from purge crystallizer 86 may be returned to water flasher 68. The bottoms of steam stripper 60 may be purged and will contain about 1 to about 391 percent of the total amount of lactam fed to this purification section.

The purified caprolactam may then be used to make polycaprolactam using a known process such as disclosed in AlliedSignal's U.S. Pat. Nos. 3,294,756; 3,558,567; or 3,579,483. The polycaprolactam may then be used in known engineered materials such as disclosed in AlliedSignal's U.S. Pat. Nos. 4,160,790; 4,902,749; or 5,162,440 or spun into fiber using a known process such as disclosed in AlliedSignal's U.S. Pat. Nos. 3,489,832; 3,517,412; or 3,619,452.

CRUDE CAPROLACTAM PREPARATION 1

A medium pressure depolymerization was performed according to commonly assigned U.S. Pat. No. 5,681,952. It was conducted in a 2 liter stirred reactor fitted with a steam inlet tube, thermocouple, and pressure control device on the vapor outlet. The vessel was preheated to 330 degrees Celsius both with external electrical heaters and by passing superheated steam through the vessel. The vessel was then filled with 800 grams of 52% type 6 nylon face fiber carpet via an extruder operating at the temperature of the reactor. Steam was passed through the reactor for 2.5 hours while the pressure was regulated to 998 KPa (130 psig) with the regulator. The vapors were condensed at atmospheric pressure. A total of 4984 grams of condensate of lactam concentration 7.3% was collected. The condensate was filtered to remove small traces of particulates and water was removed by simple distillation at atmospheric pressure to a pot temperature of 130 degrees. The contents of the distillation flask were cooled and the remainder of the water was removed at 13.3 KPa (100 Torr or mmHg) to produce a crude caprolactam concentrate which contained 1 to 2 percent water (hereinafter "Crude Caprolactam 1").

COMPARATIVE EXAMPLE 1

Crude Caprolactam 1 (91.4 g) and water (8.6 g) were mixed and heated to 60° C. to dissolve. This solution was cooled slowly to room temperature with vigorous stirring to produce crystals of caprolactam. The crystals were collected by vacuum filtration and washed three times on the filter with enough saturated caprolactam solution to just cover the crystals. The crystals were analyzed for water content. A second crystallization and washing were performed as above. The permanganate number of these crystals was 19 and the color was 29.

COMAPRATIVE EXAMPLE 2

Crude Caprolactam 1 (120 g.) was distilled at 400 Pa (3 Torr or mmHg) and 120° C. in laboratory equipment set up for simple distillation. A distillate of 96 g. was obtained. The permanganate number was 195 and the color was 98.

INVENTIVE EXAMPLE 1

Crude Caprolactam 1 (120 g.) was distilled at 400 Pa (3 Torr or mmHg) and 120° C. in laboratory equipment set up for simple distillation. A distillate of 95 g. was obtained. The contents of the distillation flask were poured from the flask at 120 degrees Celsius. The distillate was crystallized and washed by the procedure of Comparative Example 1 above. These crystals were analyzed for water content. A second crystallization and washing were performed as above. The permanganate number of these crystals was 2 and the color was 2.

CRUDE CAPROLACTAM PREPARATION 2

The procedure used to prepare Crude Caprolactam 1 was repeated 3 times except the water-caprolactam vapor from the reactor was passed to a condenser and the coolant to the condenser was adjusted such that an aqueous solution of caprolactam was condensed. The vapor which is mostly steam was condensed by a second condenser. The carpet had a nylon 6 content of 46%. The aqueous caprolactam condensates were combined and found to have a caprolactam concentration of 64%. Insoluble matter was removed and the remainder of the water was removed as described above for Crude Caprolactam 1 to make Crude Caprolactam 2 which is 98.0% caprolactam.

COMPARATIVE EXAMPLE 3

A 635 gram sample of Crude Caprolactam 2 was distilled at 1.20 KPa (9 Torr ). A distillate of 495 grams was taken which analyzes for 98.7% caprolactam. The pot temperature was 143 to 148 degrees C. Analysis of the 140 grams in the pot indicated it was only 59.6% caprolactam. This bottoms did not flow readily at 120 degrees C. The material balance for caprolactam showed that of the 622 g. at the start only 572 grams (92%) were accounted for (489 g. in the distillate and 83 g. in the pot).

INVENTIVE EXAMPLE 2

Crude Caprolactam 2 (635 grams) was distilled at 533 Pa (4 Torr). A distillate of 508 grams which analyzed for 98.7% caprolactam was taken. The pot temperature was 132 to 134 degrees Celsius. Analysis of the 127 grams in the pot indicated it was 94% caprolactam. The material in the pot flowed easily at 120 degrees. A material balance of caprolactam showed that of the 622 grams at the start 621 g.(99.8%) were accounted for (501 g. in the distillate and 119 g. in the pot).

INVENTIVE EXAMPLE 3

Crude Caprolactam 2 (635 grams) is distilled at 933 Pa (7 Torr). A distillate of 501 grams which analyzed for 98.6% caprolactam was taken. The pot temperature was 137 to 140 degrees Celsius. Analysis of the 134 grams in the pot indicated it was 88.8% caprolactam. The material in the pot flowed easily at 120 degrees. A material balance of caprolactam showed that of the 622 grams at the start 613 g (98.5%) were accounted for (494 g. in the distillate and 119 g. in the pot).

What is claimed is:

1. A process for the preparation of purified caprolactam comprising the steps of:
    (a) depolymerizing polyamide-containing carpet in the presence of steam to obtain crude caprolactam and steam;
    (b) removing substantially all of said water from said crude caprolactam and steam;
    (c) distilling the resulting concentrated crude caprolactam at a pressure of less than about 8 mmHg and a temperature from about 110° C. to about 145° C. so as to form overheads and bottoms of said caprolactam; and
    (d) crystallizing said caprolactam overheads to obtain caprolactam crystals and mother liquor.

2. The process of claim 1 wherein in said step (a), said depolymerization comprises the step of:
    in the absence of added catalyst, contacting said polyamide-containing carpet with superheated steam at a temperature of about 250° C. to about 400° C. and at a pressure within the range of about 1 atm to about 100 atm and substantially less than the saturated vapor pressure of water at the temperature wherein a caprolactam-containing vapor stream is formed.

3. The process of claim 1 wherein in said step (a), said crude caprolactam comprises water; caprolactam; 6-aminohexanoic acid; nylon 6 cyclic dimer; N-methylcaprolactam; N-ethylcaprolactam; hexenoic acid; 1,3-diphenylpropane; styrene dimer; styrene butadiene oligomers; and aliphatic alcohols and carboxylic acids with 6 to 16 carbon atoms per molecule.

4. The process of claim 1 wherein in said step (b), water is removed so that the crude caprolactam contains less than about 8 percent by weight water.

5. The process of claim 1 wherein in said step (c), the amount of said crude caprolactam distilled overhead is at least about 40 weight percent.

6. The process of claim 1 wherein in said step (c), said caprolactam bottoms are steam distilled.

7. The process of claim 1 wherein in said step (c), said caprolactam bottoms are distilled in a thin film evaporator unit.

8. The process of claim 1 wherein in said step (d), said crystallization comprises the steps of:
    (i) adjusting water in said caprolactam overheads so that the amount of said water is from about 2 weight percent to about 12 weight percent;
    (ii) dissolving said caprolactam in said water at about 35° C. to about 65° C.; and
    (iii) either cooling said mixture or evaporating sufficient water so as to form a slurry of caprolactam crystals and mother liquor wherein said crystals comprise about 25 to about 55 by weight percent of the weight of the slurry.

9. The process of claim 8 wherein said step (d) further comprises:
    (iv) removing water from said mother liquor so as to form additional caprolactam crystals; and
    (v) feeding said caprolactam crystals to said step (d)(i).

10. The process of claim 1 wherein in said step (d), at least two crystallization steps are used.

11. The process of claim 9 wherein said impurities comprise hexanoic acid; hexenoic acid; 1-hexanol, 1-octanol; N-methylcaprolactam; N-ethylcaprolactam; cyclohexylamine; and acetic acid.

12. The process of claim 1 wherein close-boiling impurities are separated from crude caprolactam in mother liquor obtained in said step (d) as overheads in a distillation operation.

13. The process of claim 1 wherein water is removed from the mother liquor of step (d) and/or the mother liquor of step (d) is cooled to obtain additional caprolactam crystals that are returned to step (d) for further purification.

14. The process of claim 1 wherein in said step (c), the temperature is from about 120° C. to about 140° C.

15. The process of claim 1 wherein in said step (c), the temperature is from about 120° C. to about 130° C.

16. The process of claim 1 wherein said purified caprolactam has a purity greater than 99.9 weight percent, permanganate number less than 3, and color number less than 2.

17. The process of claim 8 wherein said purified caprolactam has a purity greater than 99.9 weight percent, permanganate number less than 3, and color number less than 2.

18. The process of claim 9 wherein said purified caprolactam has a purity greater than 99.9 weight percent, permanganate number less than 3, and color number less than 2.

19. The process of claim 10 wherein said purified caprolactam has a purity greater than 99.9 weight percent, permanganate number less than 3, and color number less than 2.

* * * * *